(12) United States Patent
Soykan et al.

(10) Patent No.: US 8,940,522 B2
(45) Date of Patent: Jan. 27, 2015

(54) OPTICAL DETECTOR FOR USE IN THERAPY

(75) Inventors: Orhan Soykan, Shoreview, MN (US); Maura G. Donovan, St. Paul, MN (US); Amy E. Thompson, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 568 days.

(21) Appl. No.: 13/214,860

(22) Filed: Aug. 22, 2011

(65) Prior Publication Data

US 2012/0046642 A1 Feb. 23, 2012

Related U.S. Application Data

(60) Continuation of application No. 12/127,908, filed on May 28, 2008, now Pat. No. 8,003,373, which is a division of application No. 10/423,112, filed on Apr. 25, 2003, now Pat. No. 7,473,548.

(51) Int. Cl.
| | | |
|---|---|---|
| *C12M 3/00* | (2006.01) | |
| *A61B 5/145* | (2006.01) | |
| *A61B 5/00* | (2006.01) | |
| *C12Q 1/37* | (2006.01) | |
| *C12Q 1/56* | (2006.01) | |
| *G01N 21/64* | (2006.01) | |
| *G01N 21/85* | (2006.01) | |
| *G01N 33/86* | (2006.01) | |

(52) U.S. Cl.
CPC ............ *A61B 5/14546* (2013.01); *A61B 5/0071* (2013.01); *A61B 5/0075* (2013.01); *A61B 5/0084* (2013.01); *A61B 5/4839* (2013.01); *C12Q 1/37* (2013.01); *C12Q 1/56* (2013.01); *G01N 21/6428* (2013.01); *G01N 21/8507* (2013.01); *G01N 33/86* (2013.01); *A61B 5/7203* (2013.01); *G01N 2021/6415* (2013.01); *G01N 2021/6441* (2013.01); *G01N 2021/6484* (2013.01); *G01N 2021/8528* (2013.01)
USPC .................................................... 435/287.1

(58) Field of Classification Search
None
See application file for complete search history.

(56) References Cited

U.S. PATENT DOCUMENTS

| | | | |
|---|---|---|---|
| 4,146,029 A | 3/1979 | Ellingwood, Jr. | |
| 4,671,288 A | 6/1987 | Gough | |
| 4,705,503 A | 11/1987 | Dorman | |
| 4,750,494 A | 6/1988 | King | |
| 4,759,371 A | 7/1988 | Franetzki | |
| 4,890,620 A | 1/1990 | Gough | |
| 4,919,141 A | 4/1990 | Zier | |
| 5,238,809 A | 8/1993 | Wolfbeis | |
| 5,305,745 A | 4/1994 | Zacouto | |
| 5,556,421 A | 9/1996 | Prutchi | |
| 5,605,152 A | 2/1997 | Slate | |
| 5,628,310 A | 5/1997 | Rao et al. | |
| 5,756,682 A | 5/1998 | Wicks et al. | |
| 5,795,725 A | 8/1998 | Buechler et al. | |
| 5,814,524 A | 9/1998 | Walt | |
| 5,834,220 A | 11/1998 | Wicks et al. | |
| 5,914,026 A | 6/1999 | Blubaugh, Jr. | |
| 5,914,245 A | 6/1999 | Bylina | |
| 5,925,533 A | 7/1999 | Doth et al. | |
| 5,947,124 A | 9/1999 | Buechler et al. | |
| 5,964,794 A | 10/1999 | Bolz | |
| 5,981,285 A | 11/1999 | Carroll | |
| 6,002,954 A | 12/1999 | Van Antwerp | |
| 6,014,577 A | 1/2000 | Henning | |
| 6,040,194 A | 3/2000 | Chick | |
| 6,081,736 A | 6/2000 | Colvin | |
| 6,119,028 A | 9/2000 | Schulman | |
| 6,163,714 A * | 12/2000 | Stanley et al. | ................. 600/316 |
| 6,174,686 B1 | 1/2001 | Buechler | |
| 6,178,349 B1 | 1/2001 | Kieval | |
| 6,259,937 B1 | 7/2001 | Schulman | |
| 6,442,413 B1 | 8/2002 | Silver | |
| 6,451,980 B1 | 9/2002 | Khaw | |
| 6,694,158 B2 | 2/2004 | Polak | |
| 6,855,556 B2 * | 2/2005 | Amiss et al. | ..................... 436/95 |
| 7,125,660 B2 * | 10/2006 | Stanton et al. | ..................... 435/4 |
| 7,473,548 B2 * | 1/2009 | Soykan et al. | ............. 435/287.1 |
| 8,003,373 B2 * | 8/2011 | Soykan et al. | ............. 435/287.1 |

(Continued)

FOREIGN PATENT DOCUMENTS

| | | |
|---|---|---|
| DE | 3701833 | 8/1987 |
| EP | 0233108 | 8/1987 |

(Continued)

OTHER PUBLICATIONS

Kohl, et al., "A Protease Assay for Two-Photon Crosscorrelation and FRET Analysis Based Soley on Fluorescent Proteins"; Proceedings of the National Academy of Sciences, vol. 99, No. 19, (Mar. 2002), pp. 12161-121661, 8 pages.

(Continued)

*Primary Examiner* — Ann Lam
(74) *Attorney, Agent, or Firm* — Carol F. Barry; Stephen W. Bauer; Evans M. Mburu

(57) ABSTRACT

Activation of an enzyme in a bodily fluid is detected based on the amount of cleavage of a substrate for the enzyme. The substrate is tagged with two fluorescent dyes—a donor and an acceptor. The tagged substrate is presented to the bodily fluid. A device emits energy at a first wavelength into the bodily fluid, and detects energy at second and third wavelengths emitted by the dyes in response to the energy at the first wavelength. Prior to enzymatic cleavage of the substrate, the acceptor emits energy at the third wavelength in response to energy at the second wavelength received through fluorescent resonant energy transfer (FRET) from the donor. After enzymatic cleavage of the substrate, the donor emits energy at the second wavelength. The device can determine the concentration of activated enzyme within the bodily fluid based on the relative intensities of energy at the second and third wavelengths.

10 Claims, 9 Drawing Sheets

(56) References Cited

U.S. PATENT DOCUMENTS

| | | | |
|---|---|---|---|
| 2001/0025137 | A1 | 9/2001 | Webb et al. |
| 2002/0052576 | A1* | 5/2002 | Massengale ............. 604/164.01 |
| 2002/0188111 | A1 | 12/2002 | Raymond |
| 2003/0059847 | A1* | 3/2003 | Backes et al. .................. 435/7.1 |
| 2003/0113934 | A1 | 6/2003 | Kwon |
| 2003/0124622 | A1* | 7/2003 | Roemisch et al. ............. 435/7.4 |
| 2003/0134346 | A1* | 7/2003 | Amiss et al. .................... 435/14 |
| 2005/0118724 | A1* | 6/2005 | Bateman et al. .............. 436/173 |

FOREIGN PATENT DOCUMENTS

| | | |
|---|---|---|
| EP | 1342482 | 9/2003 |
| EP | 0576038 | 10/2008 |
| JP | 2000333681 A | 12/2000 |
| WO | WO 88/08992 | 11/1988 |
| WO | WO 96/30540 | 10/1996 |
| WO | WO 99/60409 | 11/1999 |
| WO | WO 00/12028 | 3/2000 |
| WO | WO 00/13748 | 3/2000 |
| WO | 0048990 A1 | 8/2000 |
| WO | WO 01/98779 | 12/2001 |
| WO | WO 02/17777 A2 | 3/2002 |
| WO | WO 02/22882 | 3/2002 |
| WO | 0230275 A1 | 4/2002 |
| WO | WO 02/078532 A1 | 10/2002 |
| WO | WO 03/020335 | 3/2003 |
| WO | WO 02/017777 A3 | 7/2003 |
| WO | WO 03/062422 | 7/2003 |

OTHER PUBLICATIONS

Ballerstadt, et al., "A Fluorescence Affinity Hollow Fiber Sensor for Continuous Transdermal Glucose Monitoring", Analytical Chemistry, vol. 72, No. 17, (Sep. 1, 2000) pp. 4185-4192; 10 pages.
JP First Office Action dated Nov. 13, 2009. 3 pages.
JP Second Office Action dated Jul. 7, 2010, 4 pages.
ACC/AHA Guidelines for the Management of Patients with Myocardial Infarction, *JACC*, 1996; 28(5):1328-1428.
Anderson et al., "Fiber Optic Immunochemical Sensor for Continuous, Reversible Measurement of Phenytoin," *Clinical Chemistry*, 1988; 34(7):1417-1421.
Becker, C. et al., "Sensitive and Specific Immunodetection of Human Glandular Kallikrein 2 in Serum," *Clinical Chemistry*, vol. 46, No. 2, p. 198-206 (2000).
Bhatia et al., "Use of Thiol-Terminal Silanes and Heterobifunctional Crosslinkers for Immobilization of Antibodies on Silica Surfaces," *Analytical Biochemistry*, 1989; 178:408-413.
Brauker et al., "Neovascularization of Synthetic Membranes Directed by Membrane Microarchitecture," *Journal of Biomedical Materials Research*, 1995: 29:1517-1524.
Braunwald, Heart Disease: A Textbook of Cardiovascular Medicine, 5th Edition, W.B. Saunders Company, Philadelphia, PA, 1997; cover page, copy right page, and p. 1189.
Braunwald, Heart Disease: A Textbook of Cardiovascular Medicine, 5th Edition, W.B. Saunders Company, Philadelphia, PA, 1997; cover page, copy right page, and p. 1126.
Braunwald, Heart Disease: A Textbook of Cardiovascular Medicine, 5th Edition, W.B. Saunders Company, Philadelphia, PA, 1997; cover page, copy right page, and p. 1290.
Chao, J. et al., "Kallistatin in a Potent New Vasodilator," *J Clin. Invest.*, vol. 100, No. 11 (1997).
Cheng, T. et al., "A Piezoelectric Quartz Crystal Sensor for the Determination of Coagulation Time in Plasma and While Blood," *Biosensors and Bioelectronics*, vol. 13, No. 2, p. 147-156 (1998).
Clegg, *Current Opinion in Biotechnology*, 1995, 6:103-110.
Delves, Antibody Application; Essential Techniques, John Wiley and Sons, 1995, cover page and p. 23.
den Braber et al., "Orientation of ECM Protein Deposition, Fibroblast Cytoskeleton, and Attachment Complex Components on Silicone Microgrooved Surfaces," *Journal of Biomedical Materials Research*, 1998; 40:291-300.

European Search Report, EP04760246.1, Jun. 15, 2007, 3 pgs.
Grant et al., "Development of Dual Receptor Biosensors: an Analysis of FRET Pairs," *Biosensors and Bioelectronics*, 2001; 16:231-237.
Grant et al., "Investigation of a FRET Immunosensor Technique for the Detection of Troponin T and I," Manuscript submitted to *Sensor Letters*, Aug. 24, 2003. Published in *Sensor Letters*, Mar. 2004; 2(1):58-63.
Grant et al., "Investigation of Labeling FRET Pairs to Biomolecules for the Development of Dual Receptor Biosensors," *Chemical and Biological Sensing*, 2000; 4036:143-150.
Hallam, P., "Interactions of Biomaterials with Cells, Proteins and Blood,", www.fractures.com/institute/teaching/talks/Biomatcells.htm, p. 1-20 (Dec. 20, 2001).
Haris, Clinical Chemistry, 4th Edition, Williams and Wilkins, Malvern, PA, 1995; pp. 289-298.
Harlow, Handling Antibodies: A Laboratory Manual, Cold Spring Harbor Laboratory Press, 1998, pp. 85-87.
Hartmann et al., "Biochemical Markers in the Diagnosis of Coronary Artery Disease," *European Heart Journal*, 1998; 19(Supplement N): N2-N7.
Hogan et al., "Medicare Beneficiaries' Costs and Use of Care in the Last Year of Life," Medicare Payment Advisory Committee, Final Report, May 1, 2000; cover page and pp. 16 and 34.
Hormone, "A Monthly Critical Overview of Current Medicine, Capsule & Comment," vol. 21, No. 9 (Sep. 15, 1997).
International Search Report, PCT/US2004/011092, Jan. 28, 2005, 5 pgs.
Ko et al., "Development of a Novel FRET Method for Detection of Listeria or Salmonella," *Sensors and Actuators B*, 2003; 96:372-378.
Koukkunen et al., "Troponin T and Creatinine Kinase Isoenzyme MB Mass in the Diagnosis of Myocardial Infarction," *Ann. Med.*, 1998; 30:488-496.
Kröger et al., "Surface Investigations on the Development of a Direct Optical Immunosensor," *Biosensors and Bioelectronics*, 1998; 13:1141-1147.
Lichlyter et al., "FRET Based Sensors Using Antibodies for the Detection of Early Markers of Infarction," A report submitted in partial fulfillment of the requirements for the degree of Master of Engineering in Biomedical Engineering, Michigan Technological University, Jul. 27, 2001; pp. 1-43.
Lichlyter, D.J. et al., "Development of a Novel FRET Immosensor Technique," *Biosensors & Bioelectronics*, vol. 19, p. 219-226 (2003).
McShane, J. et al., "Glucose Monitoring Using Implanted Fluorescent Microspheres," *IEEE-EMBS Magazine*, vol. 19, No. 6, p. 36-45 (Nov./Dec. 2000).
Penttilä et al., "Comparison of the Troponin T and Troponin I ELISA Tests, as Measured by Microplate Immunoassay Techniques, in Diagnosing Acute Myocardial Infarction," *Eur. J Clin. Chem. Clin. Biochem.*, 1997; 35(10):767-774.
Pierce et al., "Development of a FRET Based Fiber-Optic Biosensor for Early Detection of Myocardial Infarction," *Missouri Lifesciences Week 2004*, University of Missouri, Columbia, MO, Apr. 5-9, 2004; 2 pgs.
Pierce et al., "Engineering a Biosensor to Detect Cardiac Troponin I," *Biomedical Engineering Society*, Nashville, TN, Oct. 1-4, 2003; 4 pgs.
Pierce et al., "Investigation of a FRET Based Sensor Technique for the Detection of Human Cardiac Troponin T and Troponin I," *Missouri Lifesciences Week 2003*, University of Missouri, Columbia, MO, Mar. 3-7, 2003; 2 pgs.
Potyrailo, R.A. et al., "Adapting Selected Nucleic Acid Ligands (Aptamers) to Biosensors," *Analytical Chemistry*, vol. 70, No. 16, p. 3419-3425 (Aug. 15, 1998).
Rosencheim, U. et al., "Ultrasound Imaging-Guided Noninvasive Ultrasound Thrombolysis," *Circulation*, p. 238-45 (Jul. 11, 2000).
Song et al., *Anal Biochem.*, 2000, 284:35-41.
Stiene-Martin, E. et al., "Instrumentation and Quality Control in Hemostasis," *Clinical Hematology, Principles, Procedures, Correlations*, 2d ed., Ch. 58, p. 636-7, Lippincott, PA, ISBN:0-397-55321-8 (1998).
The et al., "Conjugation of Fluorescein Isothiocyanate to Antibodies, II. A Reproducible Method," *Immunology*, 1970; 18:875-881.

(56) References Cited

OTHER PUBLICATIONS

Yousef, G. et al., "The New Human Tissue Kallikrein Gene Family: Structure, Function and Association to Disease," *Endocrine Reviews*, vol. 22, No. 2, p. 184-204 (2001).

Luo et al., Application of the fluorescence resonance energy transfer method for studying the dynamics of caspase-3 activation during UV-induced apoptosis in living HeLa cells, *Biochem. Biophys. Res. Commun.*, May 2001, 283 (5):1054-60.

* cited by examiner

OPTICAL DETECTOR FOR USE IN THERAPY

This application is a continuation patent application of U.S. patent application Ser. No. 12/127,908 filed on May 28, 2008, which is a divisional of U.S. patent application Ser. No. 10/423,112 filed on Apr. 25, 2003, now U.S. Pat. No. 7,473,548 issued on Jan. 6, 2009, both of which are incorporated herein by reference.

TECHNICAL FIELD

The invention relates to medical devices, and more particularly, to medical devices that detect enzymes within bodily fluid.

BACKGROUND

In general, the activities of various enzymes within bodily fluids, such as the blood or lymph, are of clinical interest. Some enzymes exist in bodily fluids as an inactive precursor until an event or condition triggers their activation. For example, the enzymes kallikrein and thrombin are present in blood as their respective inactive precursors, prekallikrein and prothrombin, until activated. The activation of enzymes, such as kallikrein and thrombin, can indicate clinically significant underlying events or conditions.

Kallikrein is involved in the processes of signaling painful events or stimuli to the nervous system via the extrinsic pain pathway. When an agent, such as heat, force, or radiation, causes a cell to rupture, that cell releases its internal components into the surrounding environment. Among these cell components are proteins that activate kallikrein, i.e., convert inactive prekallikrein to kallikrein. Kallikrein in turn activates a protein called bradykinin, which acts on free nerve endings to signal pain in the area. Bradykinin can also induce pain by causing tissue to swell, e.g. by causing edema.

Thrombin is involved in the process of blood coagulation. Specifically, thrombin converts fibrinogen into fibrin, which in turn forms thrombi. Prothrombin is converted to thrombin as part of an intricate cascade of enzymatic activities. Generally speaking, patients with conditions that lead to pooling of the blood within vessels, such as atrial fibrillation, or patients with implanted foreign matter exposed to blood flow, such as artificial heart valves, are at increased risk of developing potentially life-threatening thrombi. Such patients often receive anticoagulants to reduce the likelihood of thrombus formation.

SUMMARY

In general, the invention is directed to techniques for optically detecting activation of an enzyme within a bodily fluid. The bodily fluid can be blood, and the detected enzyme can be, for example, kallikrein or thrombin. Activation of the enzyme can indicate a medically significant event or condition. In some embodiments, detecting activation of the enzyme within the bodily fluid according to the invention enables clinical diagnosis, chronic monitoring, and/or closed-loop therapy delivery.

Activation of the enzyme in a bodily fluid is detected based on the amount of cleavage of a substrate for the enzyme. The substrate is tagged with two fluorescent dyes, such that each of two products that will result from cleavage of the substrate by the enzyme is tagged with one of the dyes. The absorption spectrum of one of the dyes, the acceptor, overlaps the emission spectrum of the other dye, the donor.

The tagged substrate is presented to the bodily fluid. A device emits energy at a first wavelength into the bodily fluid, and detects energy, emitted by the dyes in response to the energy emitted by the device at the first wavelength, at a second and a third wavelength. The donor absorbs energy emitted by the device at the first wavelength. Prior to enzymatic cleavage of the substrate, the acceptor receives energy at the second wavelength from the donor through fluorescent resonant energy transfer (FRET), and emits energy at the third wavelength. After enzymatic cleavage, FRET does not occur and the donor emits energy at the second wavelength in response to absorbing energy at the first wavelength.

The same device that emits energy at a first wavelength can also present the tagged substrate to the bodily fluid from a reservoir using a pump and a catheter. The device can emit and detect energy via an optical fiber with a distal end located in the bodily fluid. In some embodiments, the substrate is presented to the bodily fluid on a substrate tape, or is linked to the optical fiber.

The rate of cleavage of the substrate is determined based on the relative intensities of energy at the second and third wavelengths over time. In some embodiments, the device determines a ratio between the intensities of energy at the second and third wavelengths, and determines the amount of activated enzyme within the bodily fluid based on the value of the determined ratio over time. Information describing relationships between amount of activated enzyme and ratios can be stored within a memory as one or more look-up tables, equations, curves, or the like. The amount of activated enzyme can, for example, be expressed as a concentration of activated enzyme, e.g., units per milliliter of bodily fluid. Information describing relationships between concentration of activated enzyme and ratios over time can be determined experimentally.

In some embodiments, the device stores determined amounts of activated enzyme in the memory for later retrieval by a clinician. In some embodiments, the device stores one or more thresholds in the memory and activates an alarm if the amount of activated enzyme or a rate of change of the amount of activated enzyme exceeds or falls below the threshold. Therapy, such as anticoagulant or pain relieving drug therapy, or neurostimulation, may be delivered based on determined amounts of activated enzyme.

In one embodiment, the invention is directed to a method in which energy is emitted at a first wavelength into a bodily fluid. A tagged substrate within the bodily fluid emits energy at a second wavelength and a third wavelength in response to the energy at the first wavelength, and the energy emitted by the tagged substrate is detected. Activation of an enzyme that cleaves the substrate within the bodily fluid is detected based on the detected energy. A ratio between a first detected intensity of energy at the second wavelength and a second detected intensity of energy at the third wavelength may be determined, and the concentration of activated enzyme within the bodily fluid may be determined based on the ratio.

In another embodiment, the invention is directed to a device that includes an emitting element to emit energy at a first wavelength into a bodily fluid, and a detector to detect energy emitted at a second wavelength and a third wavelength by products of a tagged substrate in the bodily fluid in response to the energy at the first wavelength. The device further includes a processor to control the emitting element to emit energy at the first wavelength, receive indications of intensities of energy detected by the detector, and detect activation of an enzyme that cleaves the substrate within the bodily fluid based on the indicated energy intensities. The device may also include an optical fiber optically coupled to the emitting element and the detector. A distal end of the optical fiber may be located in the bodily fluid. The emitting element may emit energy into the bodily fluid via the optical fiber, and the detector may detect energy emitted by products of the tagged substrate in the fluid via the optical fiber.

In another embodiment, the invention is directed to a system that includes a first medical device to optically detect activation level of an enzyme within a bodily fluid of a patient, and a second medical device to deliver a therapy to the patient based on the detection of enzyme activation. The second medical device may be, for example, a drug pump that delivers drugs to the patient based on the concentration of activated enzyme within the bodily fluid, or a neurostimulation device that delivers neurostimulation therapy to the patient based on the concentration of activated enzyme within the bodily fluid.

In another embodiment, the invention is directed to an optical fiber that includes a core and a cladding. The cladding is partially removed from a section of the fiber to expose a section of the core, and a substrate for an enzyme within a bodily fluid is linked to the exposed section of the core.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
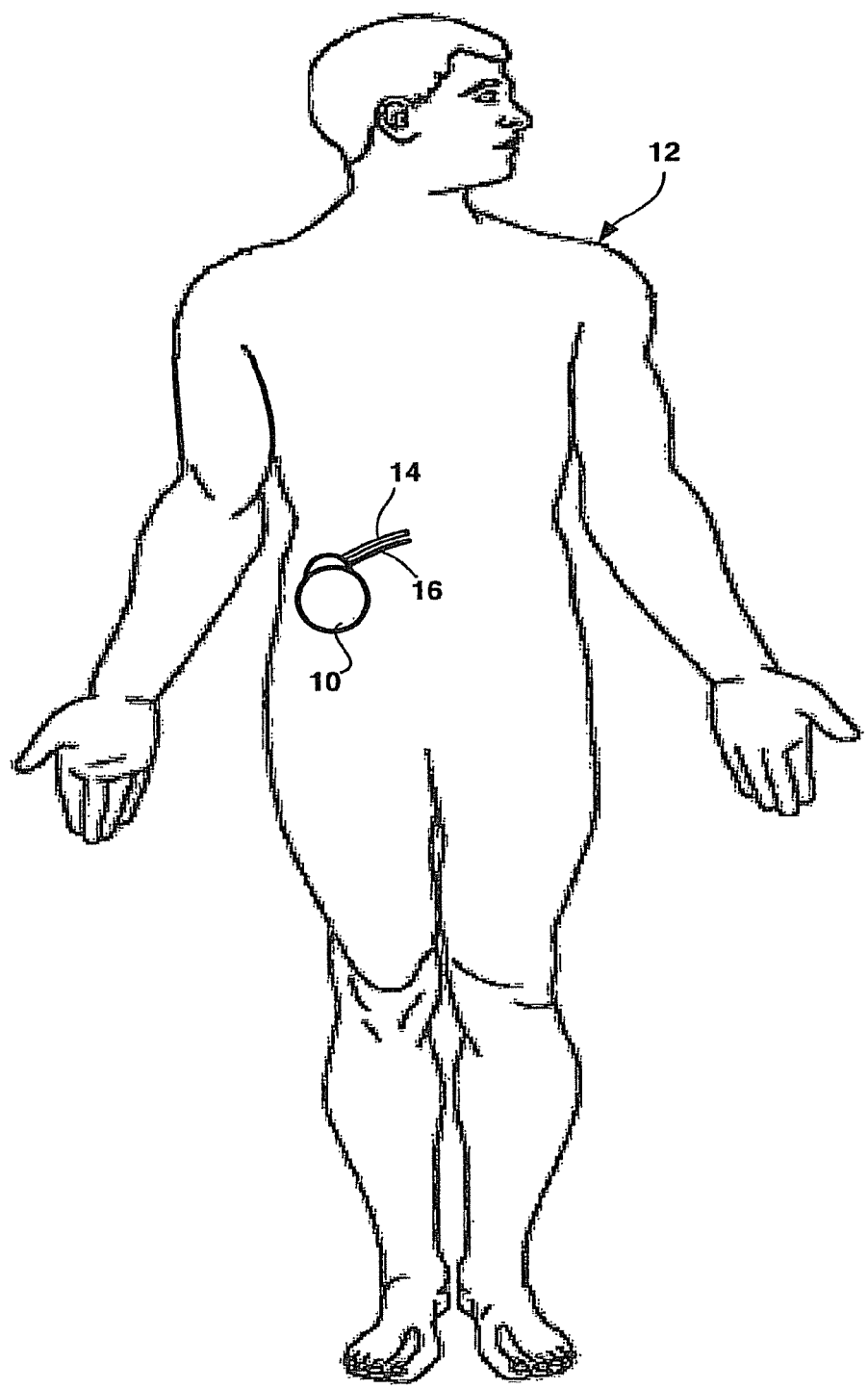
FIG. 1 is a schematic diagram illustrating an example implantable medical device for optically detecting enzyme activation.

FIG. 1 is a perspective diagram illustrating an example implantable medical device (IMD) 10 implanted within a patient 12. IMD 10 optically detects enzyme activation within a bodily fluid of patient 12. The bodily fluid can be blood within a blood vessel (not shown) of patient 12. Further, IMD 10 can, in some embodiments, detect activation of protease enzymes, such as kallikrein or thrombin, within blood.

IMD 10 is coupled to a catheter 14 and an optical fiber 16. The distal ends of catheter 16 and optical fiber 18 extend into the bodily fluid to enable IMD 12 to detect activation of the enzyme within the bodily fluid. For example, the distal ends of catheter 14 and optical fiber 16 can extend into a blood vessel so that IMD 10 can detect activation of kallikrein or thrombin within the blood of patient 12.

In general, when the target enzyme is activated within the bodily fluid, it acts to cleave a specific protein within the bodily fluid. For example, kallikrein cleaves kininogen to release bradykinin, and thrombin cleaves fibrinogen to release fibrin. According to the Michaelis-Menten model, the amount of cleaved protein depends on the concentration of activated enzyme, the turnover rate of the enzyme, and the amount of accessible protein.

IMD 10 uses a substrate to detect activation of the target enzyme. In addition to cleaving the protein, the target enzyme cleaves the substrate. IMD 10 determines the level of enzyme activation based on the extent of substrate cleavage. The substrate is presented to the bodily fluid via catheter 14.

The enzyme cleaves the protein and the substrate by breaking selected bonds within the molecular structures of the protein and the substrate. Specifically, both kallikrein and thrombin are serine-proteases and selectively target the peptide bonds between arginine and lysine or arginine and glysine. Thus, a suitable substrate for kallikrein or thrombin includes a peptide bond that can be broken by the target enzyme to cleave the substrate.

Examples of suitable substrates for kallikrein and thrombin are listed in Tables 1 and 2, respectively. However, the invention is not limited to detection of enzyme activation using these exemplary substrates. Nor is the invention limited to detection of the activation of kallikrein or thrombin. Suitable substrates for detection of the activation of any particular enzyme can be identified based on the bond selectivity of that particular enzyme.

TABLE 1

| Kallikrein Substrates |
| --- |
| H-D Pro-HHT-Arg-pNA |
| H-D-Pro-Phe-Arg-pNA |
| H-D-But-CHA-Arg-pNA.2AcOH |
| Pro-Phe-Arg-MCA |
| H-D-Val-Leu-Arg-AFC, 2HCL |

TABLE 2

| Thrombin Substrates |
| --- |
| Protein C |
| Secretin |
| Lysozyme |
| Growth Hormone |
| Actin |
| d-FPRX (where x = paranitroanilide) |
| d-FPKX (where x = paranitroanilide) |
| d-FGRX (where x = paranitroanilide) |
| d-VGKX (where x = paranitroanilide) |

IMD 10 detects the amount of substrate cleavage, and thus enzyme activation, optically. IMD 10 emits energy into the bodily fluid via optical fiber 16 when the substrate is presented to the bodily fluid. The substrate is tagged with fluorescent dyes. IMD 10 detects energy that is emitted by the fluorescent dyes in response to absorbing the energy emitted by IMD 10 via optical fiber 16. As will be described in greater detail below, IMD 10 detects the amount of substrate cleavage based on the level of fluorescent resonant energy transfer (FRET) between the dyes. The energy emitted and detected by IMD 10 may be visible light.

The distal ends of catheter 14 and optical fiber 16 can, as shown in FIG. 1, be located substantially proximate to each other within the bodily fluid. In some embodiments, catheter 14 and optical fiber 16 are contained within a common sheath (not shown) that facilitates and maintains their placement proximate to each other. However, catheter 14 and optical fiber 16 need not be collocated. For example, IMD 10 can present the tagged substrate to a blood flow via catheter 14 at a point that is "upstream" from the location of optical fiber 16. Moreover, in some embodiments IMD 10 is not coupled to a catheter 14. In such embodiments, the tagged substrate can be presented to the bodily fluid via manual injection using a hypodermic syringe and needle, via an external drug pump delivering an intravenous bolus, via a substrate tape, or linked to optical fiber 16.

Figure 2:
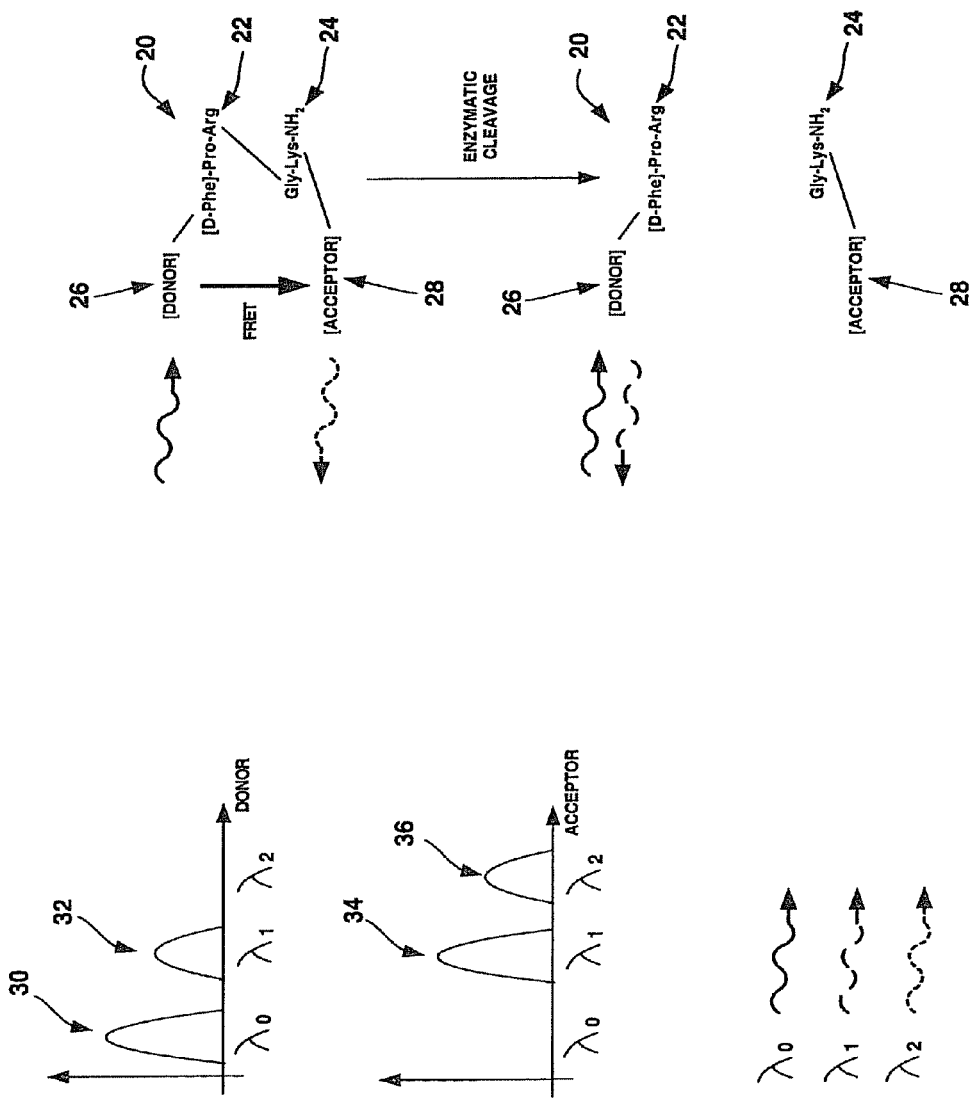
FIG. 2 is a conceptual diagram illustrating use of fluorescent resonant energy transfer to detect enzyme activation according to the invention.

FIG. 2 is a conceptual diagram illustrating use of FRET to detect enzyme activation according to the invention. An exemplary substrate molecule 20 includes a first product 22 and a second product 24. The first product 22 of substrate molecule 20 is tagged with a first fluorescent dye, which is a donor dye 26. The second product 24 of substrate molecule 20 is tagged with a second fluorescent dye, which is an acceptor dye 28.

An absorption spectrum 30 and emission spectrum 32 for donor dye 26 are illustrated in FIG. 2. An absorption spectrum 34 and emission spectrum 36 for acceptor dye 28 are also illustrated. As illustrated, donor dye 26 emits energy at a wavelength $\lambda_1$ in response to the absorption of energy at a wavelength $\lambda_0$. Acceptor dye 28 emits energy at a wavelength $\lambda_2$ in response to the absorption of energy at a wavelength $\lambda_1$. Thus, the absorption spectrum of acceptor dye 28 overlaps the emission spectrum of donor dye 26.

When donor dye 26 and acceptor dye 28 are sufficiently proximate, e.g., between approximately 10 and 100 Angstroms, and their dipole orientations are approximately parallel, acceptor 28 will resonantly receive energy at wavelength $\lambda_1$ from donor 26 via FRET. Acceptor 28 will emit energy at wavelength $\lambda_2$ in response to absorbing the energy at wavelength $\lambda_1$. As illustrated in FIG. 2, donor 26 and acceptor 28 are sufficiently proximate and properly oriented prior to enzymatic cleavage of substrate molecule 20, and acceptor 28 emits energy at wavelength $\lambda_2$ in response to donor absorbing energy at wavelength $\lambda_0$. When substrate molecule 20 is enzymatically cleaved, donor 26 and acceptor 28 are no longer sufficiently proximate or properly oriented, and donor 26 emits energy at wavelength $\lambda_1$ in response to absorbing energy at wavelength $\lambda_0$.

Figure 3:
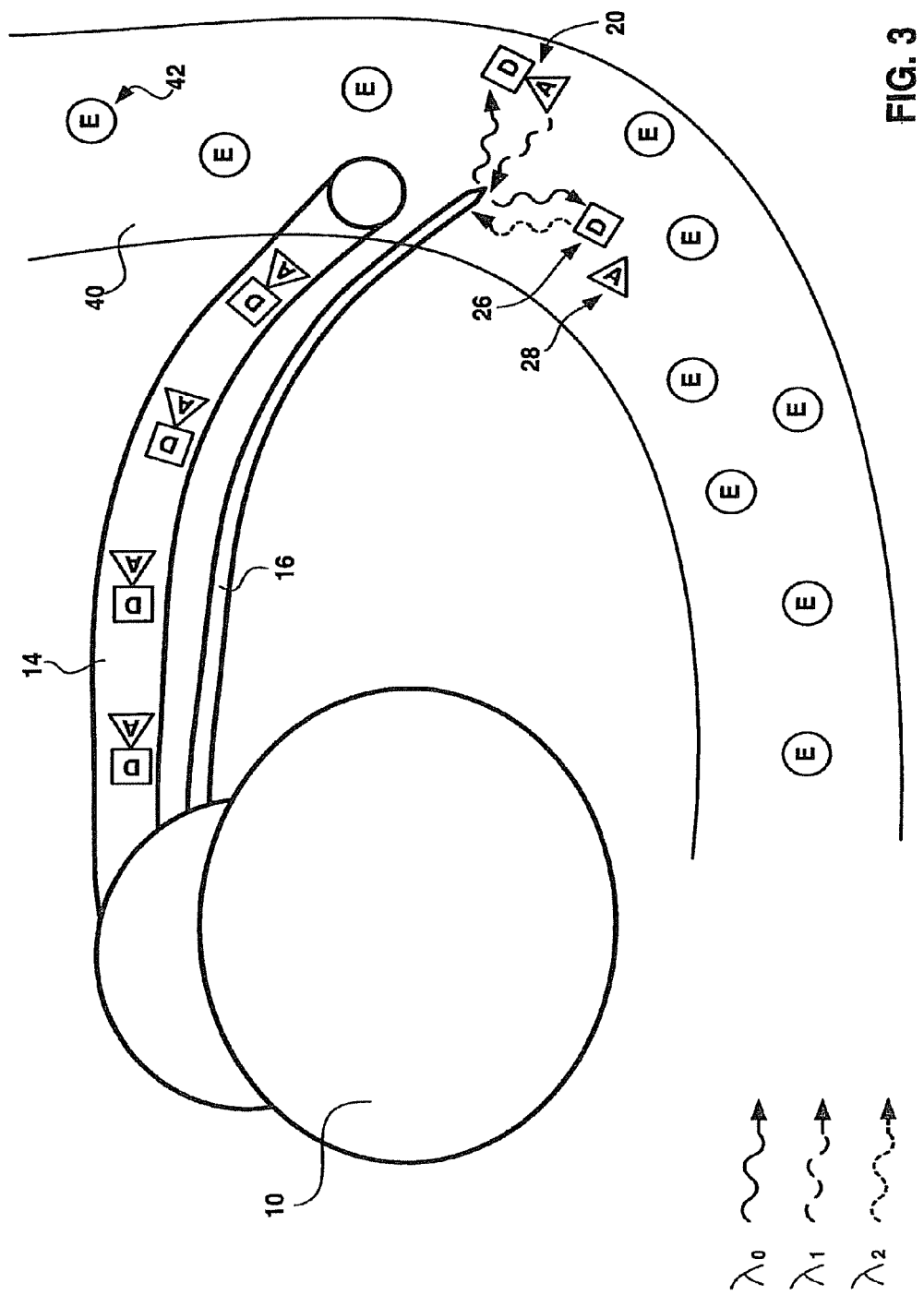
FIG. 3 is a schematic diagram illustrating an example operation of the implantable medical device of FIG. 1 to detect enzyme activation.

FIG. 3 is a perspective diagram illustrating an example operation of IMD 10 to detect enzyme activation. The distal ends of catheter 14 and optical fiber 16 are deployed within a blood vessel 40. The blood within blood vessel 40 includes enzyme 42. Enzyme 42 includes activated enzyme molecules and inactive precursor molecules for the enzyme. For example, enzyme 42 can include prekallikrein and kallikrein molecules, or prothrombin and thrombin molecules. For ease of illustration, only a single enzyme molecule 42 is labeled.

IMD 10 presents substrate 20, which includes a product tagged with donor dye 26 and a product tagged with acceptor dye 28, to the blood flow within vessel 40 via catheter 14. As shown in FIG. 3, activated enzyme molecules 42 cleave substrate 20 such that the products tagged with dyes 26 and 28 are separated. For ease of illustration, only a single substrate molecule 20 and a single instance of products tagged with donor and acceptor dye 26 and 28 are labeled.

IMD 10 emits energy at wavelength $\lambda_0$ into the blood stream of vessel 40 via optical fiber 16. Donor dye 26 absorbs energy at wavelength $\lambda_0$. When substrate molecules 20 are intact in the blood stream, acceptor dye 28 will, through FRET, emit energy at wavelength $\lambda_2$ in response to the donor 26 absorbing energy at wavelength $\lambda_0$, as described above. When activated enzyme molecules 42 cleave substrate molecules 20, dyes 26 and 28 are physically separated preventing FRET from occurring. When substrate molecules 20 are cleaved, donor 26 emits energy at wavelength $\lambda_1$ in response to absorbing the energy emitted by IMD 10 at wavelength $\lambda_0$.

IMD 10 detects energy emitted by donor 26 at wavelength $\lambda_1$ and energy emitted by acceptor 28 at wavelength $\lambda_2$ via optical fiber 16. The intensities of energy detected at wavelengths $\lambda_1$ and $\lambda_2$ are related to the amount of cleaved and uncleaved substrate 20 within vessel 40. The amount of cleaved and uncleaved substrate 20 within vessel 40 depends on the amount of activated enzyme 42 within the blood.

IMD 10 detects activation of enzyme 42 based on the ratio between the intensities of energy detected at wavelengths $\lambda_1$ and $\lambda_2$. By detecting activation of enzyme 42 based on a ratio, IMD 10 is less susceptible to errors caused by signal degradation, e.g., fibrous tissue growth on optical fiber 16. In some embodiments, IMD 10 can monitor the overall intensity of the detected energy and compensate for reduced signal intensity by increasing the intensity of the emitted energy.

Suitable donor 26/acceptor 28 pairs for use with the exemplary substrates listed in Tables 1 and 2 include AMCA/FITC and FITC/TRITC. The invention is not, however, limited to these dye pairs. Suitable dye pairs include any dye pair that has an acceptor whose absorption spectrum overlaps the emission spectrum of the donor. Suitability of a dye pair may also depend on its ability to bond to the products of a selected substrate.

Figure 4:
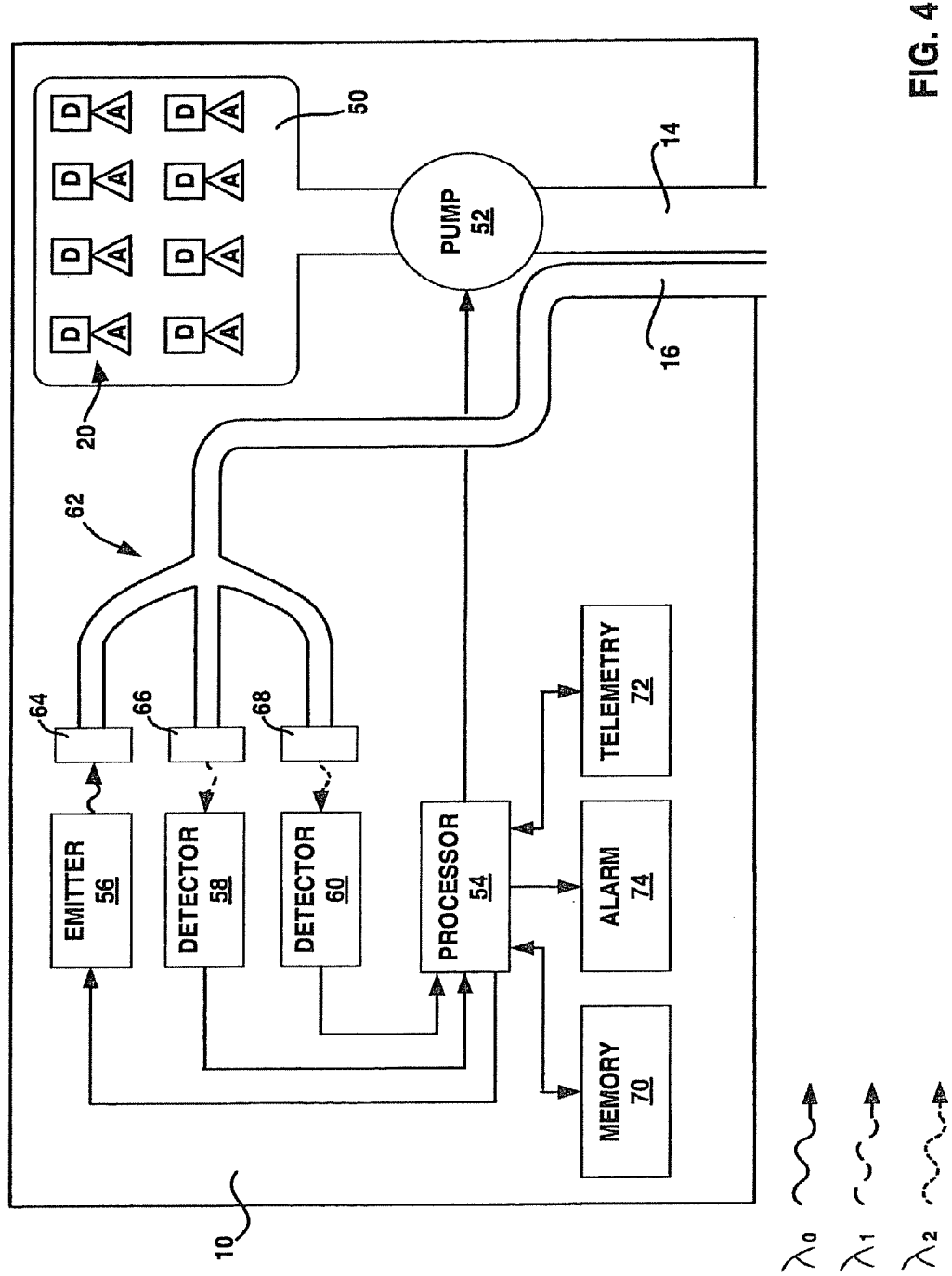
FIG. 4 is a block diagram illustrating an example configuration of an implantable medical device for optically detecting enzyme activation.

FIG. 4 is a block diagram illustrating an example configuration of IMD 10. In the example configuration of IMD 10 illustrated in FIG. 4, IMD 10 includes a reservoir 50 and a pump 52 in fluid communication with reservoir 50 and catheter 14. Reservoir 50 contains tagged substrate 20. A processor 54 controls pump 52 to present substrate 20 to bodily fluid via catheter 14. With respect to the presentation substrate 20, IMD 10 can correspond substantially to an implantable drug pump, such as Synchromed™ drug pumps sold by Medtronic Corporation. Reservoir 50 can be refillable, e.g., via a syringe, to enable chronic implantation and enzyme activation detection.

IMD 10 also includes an emitter 56 and detectors 58 and 60 that are optically coupled to optical fiber 16. Processor 54 controls emitter 56 to emit energy at wavelength $\lambda_0$ in conjunction with the presentation of substrate 20 by pump 52. Detector 58 detects energy emitted by substrate 20 in the bodily fluid at wavelength $\lambda_1$, and detector 60 detects energy emitted by substrate 20 in the bodily fluid at wavelength $\lambda_2$. Processor 54 receives an indication of the intensities of the energy at wavelengths $\lambda_1$ and $\lambda_2$ from detectors 58 and 60.

Detectors 58 and 60 can take the form of electro-optical transducers. In some embodiments, a single detector detects energy at wavelengths $\lambda_1$ and $\lambda_2$. In such embodiments, the detector can include analog or digital signal processing components in addition to an electro-optical transducer to determine the intensities at wavelengths $\lambda_1$ and $\lambda_2$ and indicate the intensities to processor 54.

An optical coupler 62 couples emitter 56 and detectors 58 and 60 the fiber 16. A filter 64 filters energy emitted by emitter 56 to assure that energy at wavelength $\lambda_0$ is delivered to the bodily fluid. Filters 66 and 68 filter energy received from substrate 20 in the bodily fluid to assure that detectors 58 and 60 receive energy at wavelengths $\lambda_1$ and $\lambda_2$, respectively. In some embodiments, filters 64-68 take the form of dichroic band-pass filters.

Energy delivered to detectors 58 and 60 can be amplified. One or more amplifiers (not shown), such chopper stabilized amplifiers, can be used to amplify the energy to improve the signal to noise ratio for the energy delivered to detectors 58 and 60.

Processor 54 detects activation of an enzyme, and can, in some embodiments, determines the amount of activated enzyme within a bodily fluid based on the indicated intensities at wavelengths $\lambda_1$ and $\lambda_2$. Specifically, processor 54 can calculate a ratio between the intensities at wavelengths $\lambda_1$ and $\lambda_2$, and determine the amount of activated enzyme based on the ratio. The amount of activated enzyme can be expressed as a concentration of the activated form of the enzyme within the bodily fluid, e.g., units per milliliter of bodily fluid.

Processor 54 can store the determined ratio in a memory 70. Memory 70 also stores information used by processor 54 to determine an amount of activated enzyme based on the ratio. For example, in some embodiments, memory 70 includes a look-up table or equation that describes a relationship between the ratio and enzyme concentration.

The determined amount of activated enzyme, e.g., concentration of activated enzyme, can be stored in memory 70 for later retrieval by a clinician. In exemplary embodiments, the clinician retrieves one or more concentrations from memory 70 using a programmer via a telemetry circuit 72, as is known in the art. Where the target enzyme is kallikrein, the clinician can use the concentrations to more accurately identify the intensity and frequency of pain, for example, and, depending on the position of optical fiber 16, the location of pain. This information may allow the clinician to more accurately diagnose the underlying cause of the pain, and prescribe more effective pain therapies for patient 12. Where the target enzyme is thrombin, the clinician can use the enzyme concentrations collected over time to, for example, better determine a dosage for anticoagulant therapy for patient 12. Telemetry can also be used to communicate information relating to the status or performance of IMD 10, such as battery and reservoir status, to clinician.

Memory 70 can store threshold values, and processor 54 can activate an alarm 74 when the ratio, concentration, rate of change of the ratio over time, or rate of change of concentration over time, exceeds or falls below a threshold value. Alarm 74 is detectable by patient 12, e.g., audibly or through vibration. Alarm 74 can be used to cause patient 12 to seek immediate medical attention when enzyme activation concentration of activated enzyme indicates an emergency medical condition, such as a thrombin concentration that indicates a dangerously high probability of thrombi formation. Increased thrombin activation can in some cases indicate a coagulation cascade preceding a heart attack.

Memory 70 can also store program instructions that control processor 54 to perform the functions ascribed to it herein. Memory 70 may include a variety of magnetic, optical, or electronic media, such as random access memory (RAM), read-only memory (ROM), electronic erasable programmable read-only memory (EEPROM), flash memory, or the like. Processor 54 may include one or more microprocessors, digital signal processors (DSPs), application specific integrated circuits (ASICs), field-programmable gate arrays (FPGAs), or the like.

In some embodiments, processor 54 controls delivery of therapy to patient 12 based on determined amounts of activated enzyme. In some embodiments, IMD 10 includes an additional reservoir, pump and catheter for the delivery of one or more drugs to patient 12. Processor 54 can control the additional pump to initiate delivery of a drug or change the dosage for a drug based on the determined amount of activated enzyme. For example, delivery of a pain relieving drug may be initiated upon determination of increased kallikrein activation, or the dosage of an anticoagulant, such as heparin, may be altered based on a determination of increased thrombin activation. In other embodiments, IMD 10 is part of system that includes a therapy delivery device that is either controlled by processor 54 or acts in response to activated enzyme amounts received from processor 54, as will be described in greater detail below. In this manner, IMD 10 can enable closed-loop delivery of therapy to patient 12.

Figure 5:
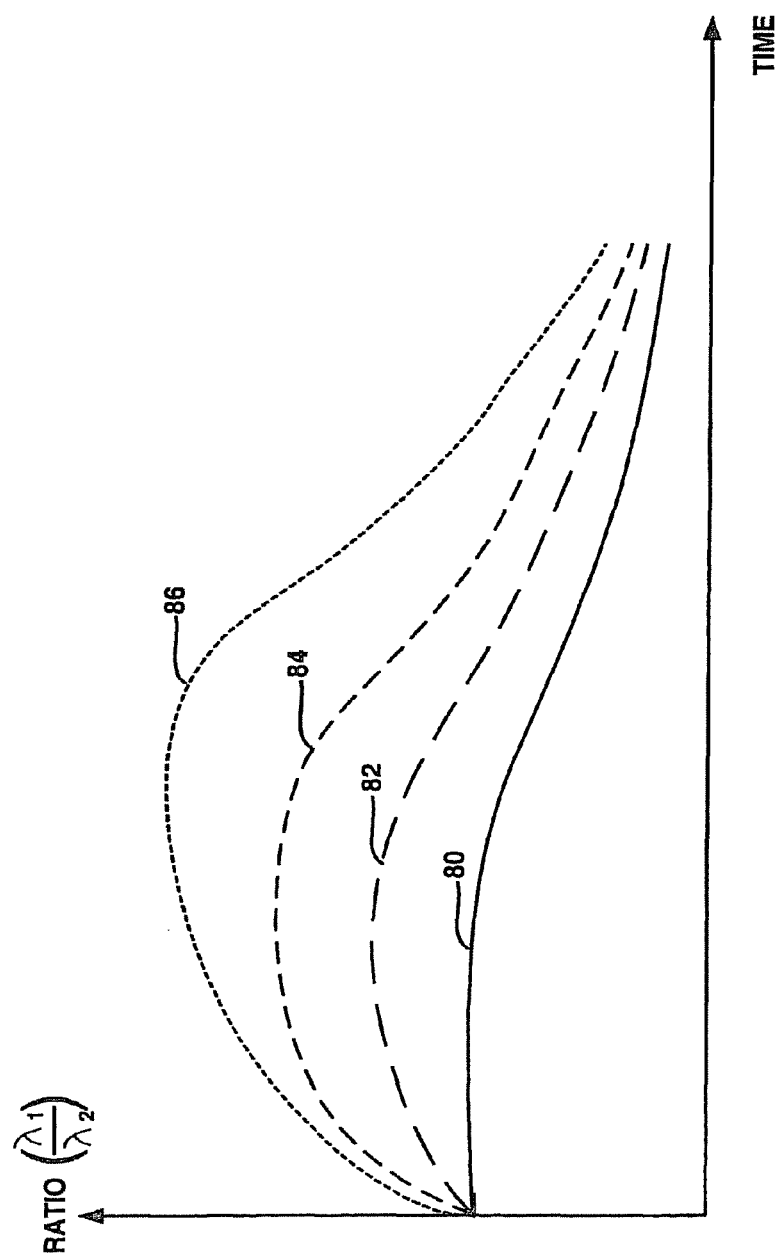
FIG. 5 is a timing diagram illustrating example ratio curves used to determine an amount of activated enzyme.

FIG. 5 is a timing diagram illustrating example ratio curves 80-86 used to determine activated enzyme amount. Each of ratio curves 80-86 is associated with an amount of activated enzyme, e.g., a concentration of activated enzyme. Ratio curves 80-86 are generated by measuring $\lambda_1/\lambda_2$ ratios over a period of time, e.g., one to ten minutes, after introduction of a known concentration of activated enzyme with a tagged substrate. In some embodiments, memory 70 stores information representing curves 80-86, and processor 54 uses the information to determine the current activation level based on one or more $\lambda_1/\lambda_2$ ratios calculated at known times subsequent to presentation of substrate 20 to the bodily fluid. The information describing curves 80-86 may be stored as one or more look-up tables or equations.

Figure 6:
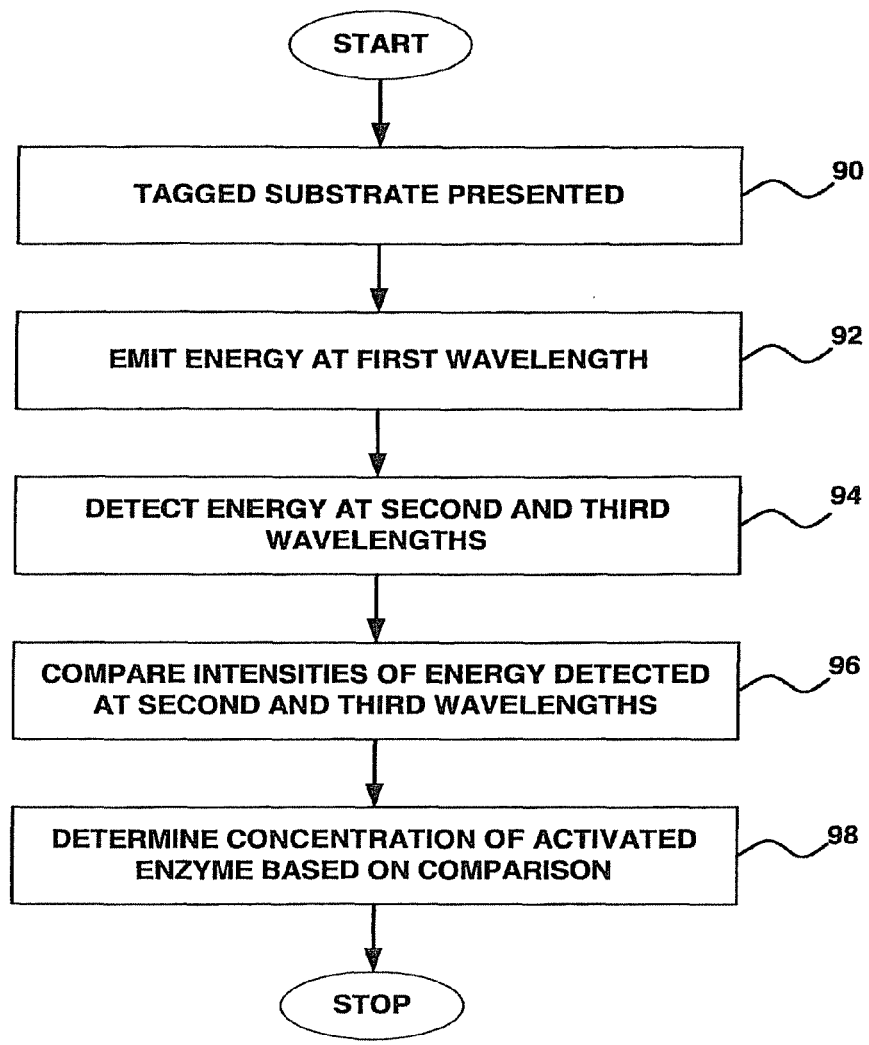
FIG. 6 is a flowchart illustrating an example method for detecting enzyme activation.

FIG. 6 is a flowchart illustrating an example method that may be employed by IMD 10 to detect enzyme activation. Tagged substrate 20 is presented to the bodily fluid (90). In some embodiments, processor 54 controls pump 52 to present substrate 20 via catheter 14, as described above. IMD 10 then emits energy at wavelength $\lambda_0$ by, for example, processor 54 controlling emitter 56 to emit energy at wavelength $\lambda_0$ (92).

IMD 10 detects energy at wavelengths $\lambda_1$ and $\lambda_2$, which is emitted by donor and acceptor dyes 26 and 28 tagged to substrate 20 in response to absorption of the energy emitted by IMD 10 at wavelength $\lambda_0$ (94). For example, in some embodiments, processor 54 receives indications of the intensities of energy at wavelengths $\lambda_1$ and $\lambda_2$ from detectors 58 and 60, as described above. Processor 54 compares the intensities of energy at wavelengths $\lambda_1$ and $\lambda_2$ (96), e.g., by calculating a $\lambda_1/\lambda_2$ ratio, and determines an amount of activated enzyme, e.g. concentration of activated enzyme, as a function of the comparison (98).

The frequency with which the method is performed can depend on the application. For example, the method can be performed one or more times during a clinic visit as a diagnostic test under the control of a clinician using a programmer. In some embodiments, the method may be performed periodically as indicated by the condition or enzyme being monitored. For example, the method may be performed one or more times per day or week, or may be performed hourly. The invention is not limited to any particular frequency of enzyme activation detection.

Figure 7:
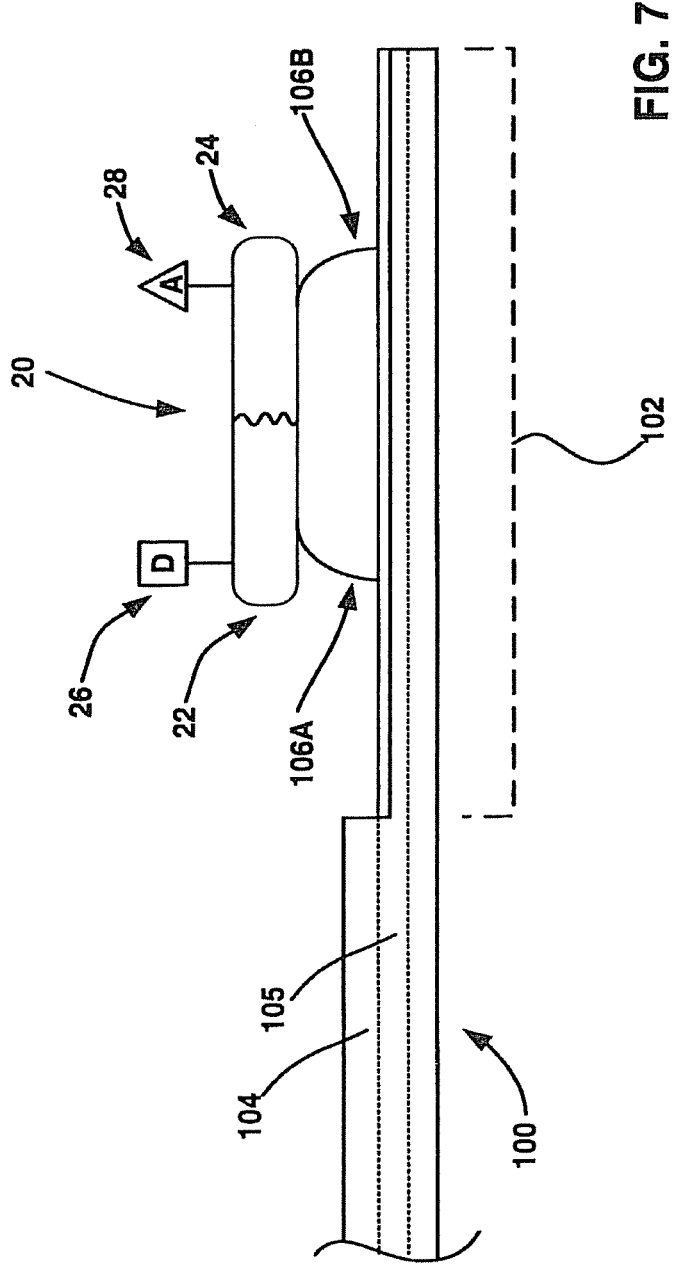
FIG. 7 is a perspective diagram illustrating an example optical fiber that includes a substrate for use in optically detecting enzyme activation.

FIG. 7 is a perspective diagram illustrating an example optical fiber 100 that can be coupled to IMD 10 according to some embodiments of the invention. As shown in FIG. 7, optical fiber 100 includes substrate 20 linked thereto. Optical fiber 100 is used to present substrate 20 to a bodily fluid. Optical fiber 100 can, for example, be used with embodiments of IMD 10 that do not include a pump 52 and reservoir 50 for presenting substrate 20 to the bodily fluid.

Substrate 20 is linked to a region 102 of optical fiber 100 where a cladding 104 of fiber 100 is partially removed to expose a core 105 of optical fiber 100. In general, cladding 104 reflects and refracts energy to direct the energy to travel within core 105 to the distal end of fiber 100. At region 102 where cladding 104 is partially removed, energy may exit and enter core 105 of fiber 100. In other words, IMD 10 may emit energy at wavelength $\lambda_0$ into a bodily fluid via region 102 such that the donor 26 presented to the bodily fluid may absorb the energy. When substrate 20 is uncleaved, as illustrated in FIG. 7, the acceptor 28 emits energy at wavelength $\lambda_2$ through FRET, as described above. The energy at wavelength $\lambda_2$ emitted by the acceptor 28 enters fiber 100 via region 102 for detection by IMD 10.

Donor tagged product 22 and acceptor tagged product 24 of substrate 20 are linked to core 105 at region 102 by cross-linkers 106A and 106B, respectively (collectively "cross-linkers 106"). Cross-linkers 106 can take the form of hetero-bifunctional cross-linkers, such as SPDP (N-Succinimidyl-3-(2-pyridyldithio)propionate). Region 102 of fiber 100 is treated with aminosilanes, such as 3-aminopropyltriethoxysilane, or proteins with modified amine groups that yield sulfhydryl-reactive intermediates to promote binding of cross-linkers 106 to region 102.

Substrate 20 is exposed to the bodily fluid, which contains an enzyme. When the enzyme cleaves substrate 20, donor tagged product 22 and acceptor tagged product 24 are separated such that FRET no longer occurs between dyes 26 and 28. The separation between donor tagged product 22 and acceptor tagged product 24 can be due in part to a springing action of cross-linkers 106. When substrate 20 is cleaved, the donor 26 will emit energy at wavelength $\lambda_1$ in response to energy emitted by IMD 10 at wavelength $\lambda_0$ via region 102, as described above.

In some embodiments, fiber 100 can be used a single time and thereafter discarded. Thus fiber 100 is particularly suitable for use with external devices capable of practicing the invention as described herein. Fiber 100 may be used percutaneously or in an in vitro sample of bodily fluid. Although it is understood that multiple substrate molecules 20 are linked to the exposed region 102, a single substrate molecule 20 is shown for ease of illustration. Further, region 102 need not be located at the distal end of fiber 100 as illustrated in FIG. 7.

Figure 8:
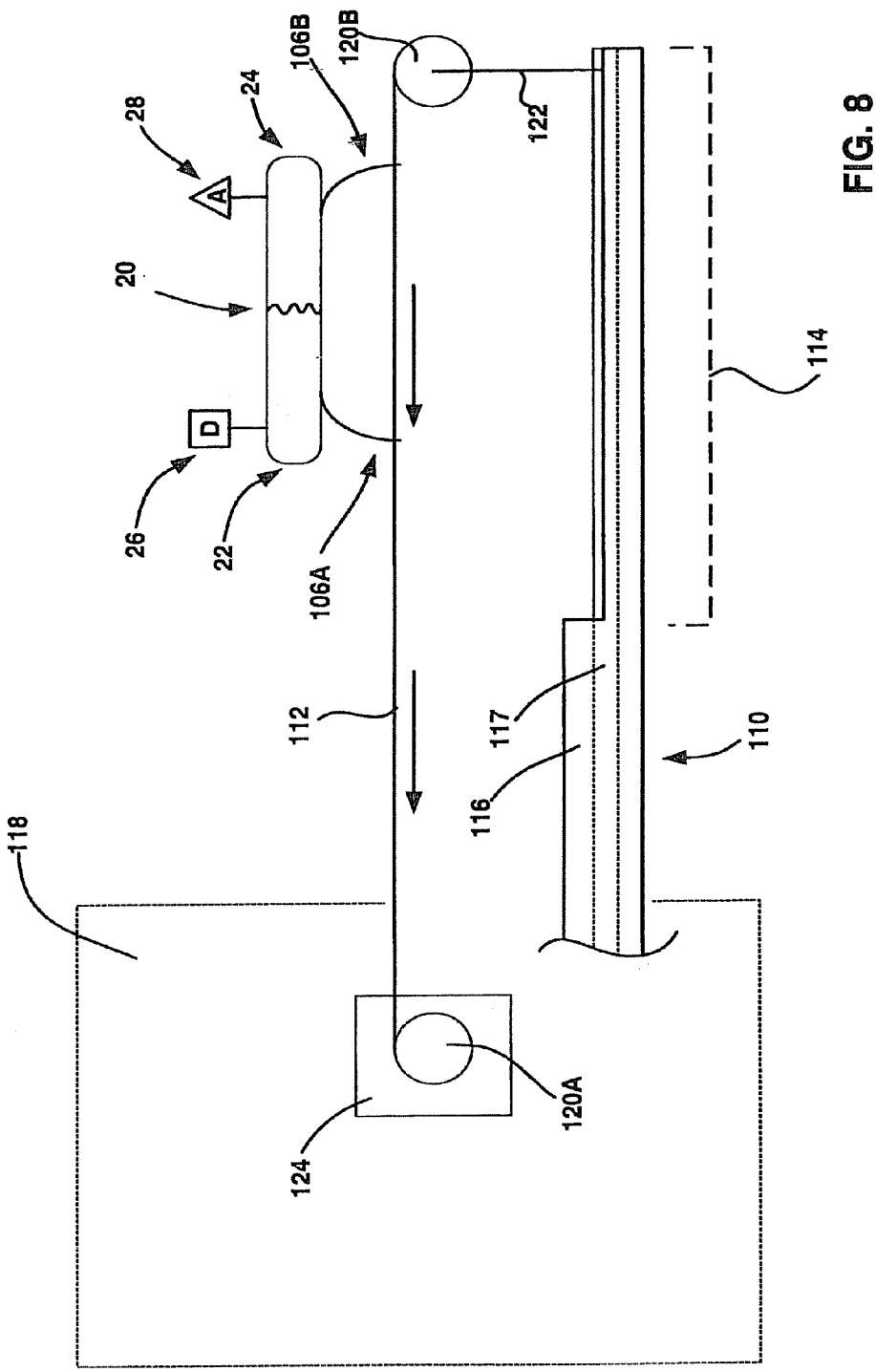
FIG. 8 is a perspective diagram illustrating an example optical fiber and a substrate tape for use in optically detecting enzyme activation.

FIG. 8 is a perspective diagram illustrating an example optical fiber 110 and a substrate tape 112 for use in optically detecting enzyme activation according to some embodiments of the invention. As shown in FIG. 8, fiber 110 may include a region 114 of optical fiber 110 where a cladding 116 of fiber 100 is partially removed to expose a core 117 of fiber 110. As described above with reference to FIG. 7, an implantable medical device 118 may emit energy and detect energy emitted by dyes 26 and 28 via region 114.

Substrate 20 is linked to tape 112 via cross-linkers 106. Tape 112 travels between reels 120A and 120B. Tape 112 can travel on a path that is substantially parallel and proximate to optical fiber 110, such the substrate 20 and dyes 26 and 28 are proximate to region 114. Reel 120B can be attached to fiber 110 by a support member 122 that allow reel 120B rotational freedom in a single direction. Reel 120A is coupled to a reel rotation mechanism 124 that rotates reel 120 to move tape 112 along the indicated path between reels 120A and 120B.

A processor (not shown) of IMD 118 can control reel rotation mechanism 124 to move tape 112 in order to present new substrate 20 for each new determination of enzyme activation. Tape 112 is spooled on reel 120B, and substrate molecules 20 are insulated from the bodily fluid while spooled on reel 120B. Substrate molecules 20 become exposed to the bodily fluid as the tape is drawn from reel 120B by the action of reel rotation mechanism 124.

IMD 118 can include components, such as a processor, emitter and detectors similar to IMD 10, as described above with reference to FIG. 4. However, for ease of illustration, only reel rotation mechanism 124 and reel 120A are shown in FIG. 8. Although it is understood that multiple substrate molecules 20 are linked to tape, a single substrate molecule 20 is shown for ease of illustration. Further, region 114 and reel 120B need not be located at the distal end of fiber 110 as illustrated in FIG. 8.

Figure 9:
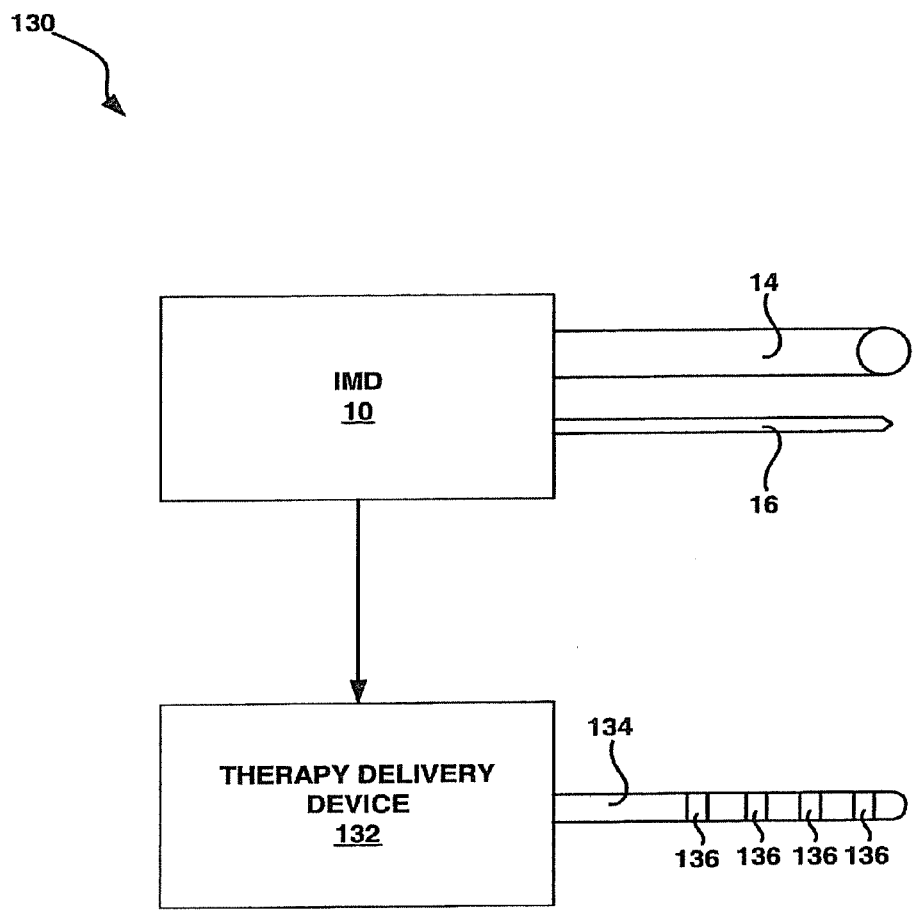
FIG. 9 is a block diagram illustrating an example system for optically determining an amount of activated enzyme and delivering therapy to a patient based on the determined amount of activated enzyme.

FIG. 9 is a block diagram illustrating an example system 130 for optically detecting enzyme activation and delivering therapy to patient 12 based on the determined level of enzyme activation. System 130 includes IMD 10 coupled to catheter 14 and optical fiber 16. IMD 10 optically determines an amount of activated enzyme as described above.

System 130 also includes a therapy delivery device 132 for delivering therapy to patient 12 based on amounts of activated enzyme as determined by IMD 10. Therapy delivery device 132 can be an implantable or external device. Therapy delivery device 132 can be, for example, an implantable drug pump that delivers a drug as a function of determined enzyme activation levels, such as a Synchromed™ drug pump. In other embodiments, therapy delivery device 132 takes the form of an implantable neurostimulation device, such as an implanted pulse generator. In such embodiments, therapy delivery device 132 delivers neurostimulation to patient 12 via one or more electrodes 136 included on a lead 134.

Drug or neurostimulation therapy can be provided to treat pain. When operated in concert with IMD 10, therapy delivery device 132 can treat pain in a closed-loop fashion, with adjustments to pain therapy based on an objective assessment of pain. In other embodiments, anticoagulation therapy is provided via a drug pump embodiment of therapy delivery device 132. In general, anticoagulant dosage is adjusted only after the coagulation status of the patient is measured, which occurs during infrequent clinic visits. Infrequently made measurements may miss changes to the condition of the patient that would require a change in the anticoagulant dosage. Too much anticoagulant can cause problematic bleeding, while too little can leave patient subject to formation of thrombi. System 130 may enable a more accurate, closed-loop determination of proper coagulation dose.

Processor 54 of IMD 10 can control therapy delivery device 132 to deliver therapy based on determined enzyme activation levels, or in other embodiments can simply communicate determined activated enzyme amounts to therapy delivery device 132 which in turn adjusts the therapy based on the communicated amounts. Processor 54 can control or communicate with device 132 via wired or RF telemetry communications. In some embodiments, IMD 10 and device 132 are a single device sharing one or more processors, or a single device with processors dedicated to either the enzyme activation detection functions or therapy delivery functions described herein.

Various embodiments of the invention have been described. For example, implantable medical devices for optically detecting enzyme activation have been described. However, one skilled in the art will recognize that the invention is not limited to the described embodiments, and that various modifications can be made to the described embodiments without departing from the scope of the invention. For example, although the invention has been primarily described herein as detecting the activation of the enzymes kallikrein and thrombin, the invention may be used to detect the activation of any enzyme within bodily fluid.

Further, although the invention has been described with reference to an implantable medical device, non-implanted embodiments are within the scope of the invention. For example, devices according to the invention can optically detect enzyme activation via percutaneous leads, or within bodily fluid samples in vitro. Some external device embodiments within the scope of the invention can utilize an optical fiber 100 linked to substrate 20 as described with reference to FIG. 7. Such embodiments may take the form of diagnostic devices within clinics for use with multiple patients or fluid samples. A new optical fiber 100 can be used for each patient or fluid sample. These and other embodiments are within the scope of the following claims.

The invention claimed is:

1. A method of delivering a therapy using an implantable medical device, comprising:
  presenting a tagged substrate into a bodily fluid, wherein the bodily fluid is blood, wherein the bodily fluid contains an enzyme and a protein substrate, and wherein presenting the tagged substrate to the bodily fluid comprises controlling a substrate pump to present the tagged substrate to the blood via a catheter with a distal end located in a blood vessel of a patient, and further wherein the tagged substrate is tagged with at least two fluorescent dyes;
  emitting energy at a first wavelength into the bodily fluid that contains the enzyme and the protein substrate, and into which the substrate tagged with the at least two fluorescent dyes has been presented;
  detecting energy emitted by a first one of the dyes at a second wavelength based on fluorescent resonant energy transfer from a second one of the dyes in response to the emitted energy at the first wavelength; and
  providing a therapy device comprising a therapy pump configured to deliver a therapy based on the detected energy.

2. The method of claim 1, wherein emitting and detecting energy comprises emitting and detecting energy via an optical fiber that includes a distal end located in a blood vessel of a patient.

3. The method of claim 1, wherein the energy is visible light.

4. The method of claim 1, wherein the enzyme is a protease enzyme.

5. The method of claim 1, further comprising:
  storing information relating to the detected energy; and
  delivering the information to a user.

6. The method of claim 1, further comprising activating an alarm in response to the detected energy.

7. The method of claim 1, wherein the method further comprises determining an amount of cleaved tagged substrate based on the detected energy, and wherein the therapy pump delivers the therapy based on the determined amount of cleaved tagged substrate.

8. The method of claim 7, further comprising detecting energy emitted by the second one of the dyes at a third wavelength in response to the emitted energy at the first wavelength, wherein determining an amount of cleaved tagged substrate comprises:
  determining a ratio between a first detected intensity of energy at the second wavelength and a second detected intensity of energy at the third wavelength, and
  determining the amount of cleaved tagged substrate within the bodily fluid based on the ratio.

9. The method of claim 8, wherein the tagged substrate includes a first product and a second product, wherein the first product is tagged with the first one of the dyes and the second product is tagged with the second one of the dyes,
  wherein the tagged substrate is cleavable by the enzyme in the bodily fluid, and
  wherein the first one of the dyes absorbs energy received from the second one of the dyes at the third wavelength via fluorescent resonant energy transfer and emits energy at the second wavelength in response to receiving the energy at the third wavelength prior to cleavage of the tagged substrate by the enzyme.

10. The method of claim 1, wherein the tagged substrate comprises a substrate similar to the protein substrate.

\* \* \* \* \*